United States Patent

(12) United States Patent
Gibson

(10) Patent No.: US 8,536,410 B2
(45) Date of Patent: Sep. 17, 2013

(54) RED SKY, VALENTINE, RED MORNING, AND SUN RISE LETTUCE VARIETIES

(75) Inventor: George D. Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 264 days.

(21) Appl. No.: 12/987,981

(22) Filed: Jan. 10, 2011

(65) Prior Publication Data

US 2011/0214210 A1    Sep. 1, 2011

Related U.S. Application Data

(60) Provisional application No. 61/294,063, filed on Jan. 11, 2010.

(51) Int. Cl.
*A01H 5/00*    (2006.01)
*A01H 5/10*    (2006.01)
*C12N 5/04*    (2006.01)

(52) U.S. Cl.
USPC ............ 800/305; 800/260; 800/298; 435/410

(58) Field of Classification Search
None
See application file for complete search history.

(56) References Cited

U.S. PATENT DOCUMENTS 7,453,027 B1 *    11/2008    Knerr ............................ 800/305

* cited by examiner

*Primary Examiner* — Eileen B O Hara
(74) *Attorney, Agent, or Firm* — Morrison & Foerster LLP

(57) ABSTRACT

New lettuce varieties designated Red Sky, Valentine, Red Morning, and Sun Rise are described. Red Sky, Valentine, Red Morning, and Sun Rise are Red Leaf lettuce varieties exhibiting stability and uniformity.

24 Claims, No Drawings

US 8,536,410 B2

RED SKY, VALENTINE, RED MORNING, AND SUN RISE LETTUCE VARIETIES

I. CROSS REFERENCE TO RELATED APPLICATIONS

This application claims the benefit under 35 USC 119(e) of prior U.S. Provisional Patent Application No. 61/294,063, filed Jan. 11, 2010, the disclosure of which is hereby incorporated by reference in its entirety.

II. FIELD OF THE INVENTION

This invention relates to the field of plant breeding. In particular, this invention relates to a group of new lettuce, *Lactuca sativa*, varieties, Red Sky, Valentine, Red Morning, and Sun Rise.

III. BACKGROUND OF THE INVENTION

Baby leaf lettuce or spring mix lettuce is an increasingly popular crop. Worldwide baby leaf lettuce consumption continues to increase. As a result of this demand, there is a continued need for new baby leaf lettuce varieties. In particular, there is a need for improved Red Leaf lettuce varieties that exhibit darker red color, have improved resistance to Downy mildew, have a thicker leaf texture, and have increased weight and yield.

IV. SUMMARY OF THE INVENTION

In order to meet these needs, the present invention is directed to improved Red Leaf lettuce varieties that exhibit vigorous growth, increased weight and yield. In particular, the present invention is directed to *Lactuca sativa* seed designated as Red Sky having ATCC Accession Number PTA-11666. The present invention is further directed to a *Lactuca sativa* plant produced by growing Red Sky lettuce seed having ATCC Accession Number PTA-11666. The present invention is further directed to a *Lactuca sativa* plant having all the physiological and morphological characteristics of a *Lactuca sativa* plant produced by growing Red Sky lettuce seed having ATCC Accession Number PTA-11666. The present invention is further directed to an $F_1$ hybrid *Lactuca sativa* plant having Red Sky as a parent wherein Red Sky lettuce seed is grown from Red Sky seed having ATCC Accession Number PTA-11666.

The present invention is further directed to pollen isolated from Red Sky lettuce plants. The present invention is further directed to tissue culture of Red Sky lettuce plants.

The present invention is further directed to a method of selecting lettuce comprising a) growing Red Sky lettuce plants wherein the plants are grown from lettuce seed having ATCC Accession Number PTA-11666 and b) selecting a plant from step a). The present invention is further directed to lettuce plants and seeds produced there from wherein the lettuce plant is isolated by the selection method of the invention.

The present invention is further directed to a method of breeding lettuce comprising crossing a lettuce plant with a plant grown from Red Sky lettuce seed having ATCC Accession Number PTA-11666. The present invention is further directed to lettuce plants and seeds produced there from wherein the lettuce plant is isolated by the breeding method of the invention.

In another embodiment, the present invention is directed to *Lactuca sativa* seed designated as Valentine having ATCC Accession Number PTA-11668. The present invention is further directed to a *Lactuca sativa* plant produced by growing Valentine lettuce seed having ATCC Accession Number PTA-11668. The present invention is further directed to a *Lactuca sativa* plant having all the physiological and morphological characteristics of a *Lactuca sativa* plant produced by growing Valentine lettuce seed having ATCC Accession Number PTA-11668. The present invention is further directed to an $F_1$ hybrid *Lactuca sativa* plant having Valentine as a parent wherein Valentine lettuce seed is grown from Valentine seed having ATCC Accession Number PTA-11668.

The present invention is further directed to pollen isolated from Valentine lettuce plants. The present invention is further directed to tissue culture of Valentine lettuce plants.

The present invention is further directed to a method of selecting lettuce comprising a) growing Valentine lettuce plants wherein the plants are grown from lettuce seed having ATCC Accession Number PTA-11668 and b) selecting a plant from step a). The present invention is further directed to lettuce plants and seeds produced there from wherein the lettuce plant is isolated by the selection method of the invention.

The present invention is further directed to a method of breeding lettuce comprising crossing a lettuce plant with a plant grown from Valentine lettuce seed having ATCC Accession Number PTA-11668. The present invention is further directed to lettuce plants and seeds produced there from wherein the lettuce plant is isolated by the breeding method of the invention.

In a further embodiment, the present invention is directed to *Lactuca sativa* seed designated as Red Morning having ATCC Accession Number PTA-11669. The present invention is further directed to a *Lactuca sativa* plant produced by growing Red Morning lettuce seed having ATCC Accession Number PTA-11669. The present invention is further directed to a *Lactuca sativa* plant having all the physiological and morphological characteristics of a *Lactuca sativa* plant produced by growing Red Morning lettuce seed having ATCC Accession Number PTA-11669. The present invention is further directed to an $F_1$ hybrid *Lactuca sativa* plant having Red Morning as a parent wherein Red Morning lettuce seed is grown from Red Morning e seed having ATCC Accession Number PTA-11669.

The present invention is further directed to pollen isolated from Red Morning lettuce plants. The present invention is further directed to tissue culture of Red Morning lettuce plants.

The present invention is further directed to a method of selecting lettuce comprising a) growing Red Morning lettuce plants wherein the plants are grown from lettuce seed having ATCC Accession Number PTA-11669 and b) selecting a plant from step a). The present invention is further directed to lettuce plants and seeds produced there from wherein the lettuce plant is isolated by the selection method of the invention.

The present invention is further directed to a method of breeding lettuce comprising crossing a lettuce plant with a plant grown from Red Morning lettuce seed having ATCC Accession Number PTA-11669. The present invention is further directed to lettuce plants and seeds produced there from wherein the lettuce plant is isolated by the breeding method of the invention.

In yet another embodiment, the present invention is directed to *Lactuca sativa* seed designated as Sun Rise having ATCC Accession Number PTA-11667. The present invention is further directed to a *Lactuca sativa* plant produced by growing Sun Rise lettuce seed having ATCC Accession Number PTA-11667. The present invention is further directed to a *Lactuca sativa* plant having all the physiological and morphological characteristics of a *Lactuca sativa* plant produced by growing Sun Rise lettuce seed having ATCC Accession Number PTA-11667. The present invention is further directed to an $F_1$ hybrid *Lactuca sativa* plant having Sun Rise as a parent wherein Sun Rise lettuce seed is grown from Sun Rise seed having ATCC Accession Number PTA-11667.

The present invention is further directed to pollen isolated from Sun Rise lettuce plants. The present invention is further directed to tissue culture of Sun Rise lettuce plants.

The present invention is further directed to a method of selecting lettuce comprising a) growing Sun Rise lettuce plants wherein the plants are grown from lettuce seed having ATCC Accession Number PTA-11667 and b) selecting a plant from step a). The present invention is further directed to lettuce plants and seeds produced there from wherein the lettuce plant is isolated by the selection method of the invention.

The present invention is further directed to a method of breeding lettuce comprising crossing a lettuce plant with a plant grown from Sun Rise lettuce seed having ATCC Accession Number PTA-11667. The present invention is further directed to lettuce plants and seeds produced there from wherein the lettuce plant is isolated by the breeding method of the invention.

V. DETAILED DESCRIPTION OF THE INVENTION

In order to more clearly understand the invention, the following definitions are provided:

Red Leaf Lettuce: Red Leaf lettuce, *Lactuca sativa*, is most often grown as 'baby leaf' or 'spring mix' and its leaves are often included in salad mixes. Red Leaf lettuce, grown for spring mix or baby leaf is a lettuce plant type that forms elongated leaves often with narrow petioles and a leaf margin that can vary from smooth to highly filled. The anthocyanin concentration of a Red Leaf lettuce can also vary between varieties, and can be either slightly concentrated producing a light red and green leaf color, or highly concentrated, producing a darker Red Leaf with minimal green color. A Red Leaf lettuce that has a lighter concentration of anthocyanin is referred to as a 'single' or 'double red', where as a Red Leaf lettuce variety with a high anthocyanin concentration is referred to as 'triple red'. The single, double or triple notation refers to the number of anthocyanin controlling genes present in the particular variety of Red Leaf lettuce.

Spring Mix: Spring mix lettuce refers to lettuce that is grown in high concentrations and harvested at a very young or 'baby leaf' stage, typically 30 to 45 days after planting. The plantings are often done on wider 80 to 84 inch beds and often contain up to one million plants per acre. Compared to iceberg or romaine plantings, where they are typically harvested 60 to 100 days after planting, with a population of roughly 25,000 to 30,000 plants per acre. Spring mix plantings often include multiple types of lettuces, all harvested when the leaves are young and tender. These plantings can include green romaine, red romaine, dark lolla rossa, tango, green leaf, and Red Leaf types. Spring mix fields are most often harvested mechanically and the harvested leaves are packed in plastic totes, where they are transported to a processing facility where they are washed, processed and mixed according to the salad recipe.

Downy mildew: Downy mildew (Dm) is a foliar disease caused by *Bremia lactucae*, an obligate fungal-like parasite. Cool, moist conditions are necessary for disease development. Free moisture on the leaf surface is essential for spore germination and infection, but not growth of the pathogen within the leaf. Initial symptoms are pale yellow regions on the upper side of older leaves with corresponding white fluffy growth, the spores of the pathogen, on the lower leaf surface Infected areas are limited by leaf veins. Infected tissue turns brown. Infection stops when temperatures rise above the disease optimum of 50°-72° F. and free moisture from rain, irrigation or dew is absent.

The disease is managed by planting varieties of lettuce with tolerance and resistance and with preventative application of fungicides. Fungicides should be applied when there is a period of cool, moist weather.

Due to the dense plant populations and the fact that lettuce grown for spring mix is often grown organically there in increased disease pressure from Downy mildew. The dense plant populations as described above limit the air flow between the plants creating a more ideal environment for Downy mildew to grow on the lettuce leaves. When grown organically, the common pesticides that are used to control Downy mildew cannot be applied there fore increasing the need for genetic resistance with in the varieties. When Downy mildew infects a plant it results in fluffy white sporulation that develops into yellow lesions rendering the leaf unmarketable.

There have been multiple resistance genes identified in lettuce that provide resistance to many of the different pathotypes of Downey mildew. These resistance genes have been identified by institutions such as the USDA, ARS, and UC Davis.

The disease which is caused by the fungus *Bremia lactucae* Regel is known as Downy mildew. Downy mildew occurs worldwide and represents a great problem for both the yield and quality of cultivated lettuce. The fungus can infect the lettuce plant at any stage of growth, after which the first symptoms of Downy mildew consist of the appearance of chlorotic yellow spots on the leaf surface. Within 24 to 48 hours a white fluffy fungus growth then becomes visible and the lower leaf surface as an indication of spore formation. During the infection the lesions become increasingly larger and more chlorotic until the leaves become completely brown.

*Bremia lactucae* is one of the so-called Oomycetes, a class of relatively primitive fungi. Other known fungi of this group are for instance *Phytium* and *Phytophtora*. The fungus *B. lactucae* contains different physiological species ("physios") and is host-specific. *Bremia lactucae* is known as a very variable pathogen. New physios occur relatively frequently through mutation of the avirulence genes during the spore formation preceding the propagation of *B. lactucae*.

A large number of Dm-resistance genes have already been identified which can bring about resistance to specific physics of *Bremia lactucae* Regel. Genetic research has shown that these Dm-resistance genes often occur clustered in groups on the same chromosome. Four such linking groups on different chromosomes in the genome of lettuce have been demonstrated which contain different Dm-resistance genes (Farrara et al., Plant Pathology 36, 499-514, 1987). Newly identified Dm-genes can often be classified into one of the known resistance linking groups.

Rogueing: Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Taking into account these definitions, the present invention is directed to seeds of the lettuce varieties Red Sky, Valentine, Red Morning, and Sun Rise; plants produced by growing Red Sky, Valentine, Red Morning, and Sun Rise seeds; plants selected from a collection of Red Sky, Valentine, Red Morning, and Sun Rise plants and seeds derived or produced therefrom; and plants produced by crossing a lettuce plant with a Red Sky, Valentine, Red Morning, or Sun Rise lettuce plant and seeds derived or produced therefrom.

VI. ORIGIN AND BREEDING HISTORY OF THE VARIETY RED SKY

Red Sky is a Red Leaf lettuce variety developed from a hand pollinated cross of the red Batavia cultivar Carnival, a Progeny Advanced Genetics variety, and the Dark Lolla Rossa cultivar Revolution. The initial cross was made in a San Joaquin valley research and development seed production field in Year 1. The F1 seed harvested was designated as PSJV032055XPSJV032066. Carnival, a medium sized, open growing, heavily textured single red Batavia lettuce type was selected as a source of improved heavier and thicker leaf texture, increased leaf weight, its slow growth habit, and its adaptability to warmer lettuce production areas and time periods. Revolution was selected for its triple red color, increased resistance to Downy mildew and its more frilled leaf margin. By implementation of single seed descent and the pedigree selection breeding methods we developed a triple red, Downy mildew resistant Red Leaf variety with thicker textured and heavier leaves. Red Sky is resistant to multiple pathotypes of Downy mildew, including dm pathotypes 1-16, 21, 23, and 24.

Following harvest of the F1 seeds, approximately 50 plants of the F1 seed were immediately planted in a research green house for seed increase late in Year 1. The F2 seed was harvested in mass in the spring of Year 2 and labeled PSJB032392.

A population of roughly 100 F2 plants labeled PSJV043058 was planted in a research and development seed production field in the spring of Year 2. One hundred individual F2 plants were randomly selected and harvested individually when the seed reached maturity. The individual F3 plants harvested were cleaned and processed and labeled in individual envelopes as PSJV043058-1 through PSJV043058-100. One seed from each envelope was removed randomly and placed in a new envelope labeled PAUS043619.

The 100 seeds labeled PAUS043619 were sent to Australia and grown in a research seed production field during the northern hemisphere winter of Year 2 to Year 3. Again, at seed maturity, all 100 plants were harvested, processed and packaged individually. The F4 seed was shipped back to the US, where 100 packets labeled PAUS043619-1 through PAUS043619-100 were received.

Fifty plants from each F4 line were planted in seedling trays, along side parent and standard Red Leaf varieties. After roughly 2 weeks of green house growth the plants were moved out doors to develop their true leaf color and texture. After roughly 40 days of growth the lines were evaluated for uniformity, color, leaf type, leaf frill, leaf thickness and leaf weight. The F4 lines that exhibited the best combination of these traits were selected and noted. The advancements included line number PAUS043619-26.

Roughly 100 seeds of PAUS043619-26 were then planted in a green house research facility, under the designation PSJB054586 in the fall of Year 3. The 100 plants were rogued at the rosette stage of maturity and any off types were removed. The remainder of the plants was allowed to grow to complete seed maturity and the F5 seed was harvested in mass in the spring of Year 4. This F5 line, selected F5 sister lines and the parent lines were grown and evaluated in multiple green house and field trials in Year 4. The lines were evaluated based on uniformity, color, leaf type, leaf frill, leaf thickness and leaf weight. The lines that best demonstrated the combined traits were noted and advanced.

While the trials of the F5 lines were being conducted and evaluated, the F6 seed increase was being conducted simultaneously in a summer Year 4 research seed production field. Line PSJB054586 was redesignated as PSJV065030, and 1000 plants were planted for seed increase. The F5 line was rogued at multiple stages of development and any noted offtypes were removed. The remaining plants were harvested in mass in the fall of Year 4.

Multiple large scale trials of PSJV065030, its advanced sister lines and its parent lines were again conducted and evaluated in Year 5. The trials were evaluated, and the lines that expressed the best combination of desired leaf color, leaf type, leaf frill, leaf thickness and leaf weight were advanced, including PSJV065030.

Again, additional seed increases were made of the lines while the trials were being conducted during the summer of Year 5. Line PSJV065030 was redesignated PSJV075458 and 2000 plants were grown in a research and development seed production field for seed increase. The F7 seed was harvested in mass in the fall of Year 5.

All lines that were advanced from the Year 5 trialing process were then screened for resistance to Downy mildew by a commercial laboratory. Line PSJV075458, along with multiple advanced sister lines were screened. PSJV075458 was determined to be resistant to Downy mildew pathotypes 1-16, 21 and 24.

Based on trialing and the disease screening results, the item PSJV075458 was advanced and designated as PX 124 in the fall of Year 5.

PX 124 was again increased in a Year 6 commercial seed production block in the San Joaquin valley. The variety was evaluated and noted to be uniform, stable and free of variants. The F8 seed was harvested in mass in the late summer of Year 6. Additional trialing of F8 seed for was conducted in Year 6 and Year 7.

PX 124 was named 'Red Sky' in the fall of Year 6.

As evaluated in seed production and field trials, the F7 and the F8 seed from the variety Red Sky has been uniform and stable with out variants.

A. Variety Description Information Red Sky

| | |
|---|---|
| Plant Type: | Red Leaf |
| Seed: | |
| Seed Color: | White |
| Light Dormancy: | No |
| Heat Dormancy: | Yes |
| Cotyledons: | |
| Shape of Cotyledons: | Spatulate |
| Shape of Fourth Leaf: | Elongated |
| Length/Width Index of Fourth Leaf: | 20 |
| Apical Margin: | Moderately Dentate |
| Basal Margin: | Moderately Dentate |
| Undulation: | Medium |
| Green Color: | Medium |
| Anthocyanin: | |
| Distribution: | Spotted |
| Rolling: | Present |

-continued

| | |
|---|---|
| Cupping: | Slight |
| Reflexing: | Apical Margin |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Medium |
| Anthocyanin | |
| Distribution: | Throughout |
| Size: | Medium |
| Glossiness: | Medium |
| Blistering: | Absent |
| Leaf Thickness: | Thick |
| Trichomes: | Absent |

B. Comparison to Most Similar Variety

| Characteristic | Red Sky | Carnival | Revolution |
|---|---|---|---|
| Spread of Frame Leaves | 18 | 26 | 18 |
| Head Diameter (market trimmed with single cup leaf) | N/A | 12 cm | N/A |
| Head Shape | Open | Upright | Open |
| Head Size Class | Small | Medium | Small |
| Head Count per Carton | N/A | N/A | N/A |
| Head Weight | N/A | 450 g | N/A |
| Head Firmness | N/A | N/A | N/A |
| Butt | | | |
| Shape | Pointed | Rounded | Pointed |
| Midrib | Flat | Moderately raised | Flat |
| Core (Stem of Market-trimmed Head) | | | |
| Diameter at the base of the Head | N/A | 4.5 cm | N/A |
| Ratio of Head Diameter/Core Diameter | N/A | 2.6 | N/A |
| Core Height from base of Head to Apex | N/A | 3.5 cm | N/A |
| Number of Days from First Water Date to Seed Stalk Emergence (Summer condition) | 50 | 66 | 48 |
| Bolting Class | Fast | Slow | Fast |
| Height of Mature Seed Stalk | 122 cm | 119 cm | 118 cm |
| Spread of Bolter Plant | 28 cm | 30 cm | 19 cm |
| Bolter Leaves | Curved | Straight | Curved |
| Margin | Dentate | Entire | Dentate |
| Color | Medium Red | Green/red | Dark Red |
| Bolter Habit | | | |
| Terminal Inflorescence | Absent | Absent | Absent |
| Lateral Shoots (above head) | Absent | Absent | Absent |
| Basal Side Shoots | Absent | Absent | Absent |
| Adaptation Regions | | | |

C. Growing Season

| Season | Red Sky | Carnival | Revolution |
|---|---|---|---|
| Spring area | All Coastal and Desert regions | All Coastal and Desert regions | All Coastal and Desert regions |
| Summer area | All Coastal regions | All Coastal regions | All Coastal regions |
| Fall area | All Coastal and Desert regions | All Coastal and Desert regions | All Coastal and Desert regions |
| Winter area: | All Desert regions | All Desert regions | All Desert regions |

D. Diseases and Stress Reactions

| Disease or Stress | Red Sky | Carnival | Revolution |
|---|---|---|---|
| Virus | | | |
| Big Vein: | Susceptible | Susceptible | Susceptible |
| Lettuce Mosaic: | Resistant | Resistant | Resistant |

E. Fungi/Bacteria

| Fungal/Bacterial | Red Sky | Carnival | Revolution |
|---|---|---|---|
| Corky Root Rot (*Pythium* Root Rot): | Susceptible | Susceptible | Susceptible |
| Downy Mildew | Resistant bl 1-16, 21, 23 and 24, CA V-VIII | Ca I, II, III | bl 1-16, 21, 23 and CA I-VI |
| Powdery Mildew: | Susceptible | Susceptible | Susceptible |
| Sclerotinia Rot: | Susceptible | Susceptible | Susceptible |
| Bacterial Soft Rot (*Pseudomonas* spp. & others): Not tested | Susceptible | Susceptible | Susceptible |
| *Botrytis* (Gray Mold): | Susceptible | Susceptible | Susceptible |
| Other: Corky Root Rot (*Rhizomonas suberifaciens*): | Susceptible | Susceptible | Susceptible |

F. Insects

| Insects | Red Sky | Carnival | Revolution |
|---|---|---|---|
| Cabbage Loopers: | Susceptible | Susceptible | Susceptible |
| Root Aphids: | Susceptible | Susceptible | Susceptible |
| Green Peach Aphid: | Susceptible | Susceptible | Susceptible |

G. Physiological/Stress

| Stress | Red Sky | Carnival | Revolution |
|---|---|---|---|
| Tipburn | N/A | Resistant | N/A |
| Heat | Susceptible | Resistant | Susceptible |
| Drought | Susceptible | Susceptible | Susceptible |
| Cold | Susceptible | Susceptible | Susceptible |
| Salt | Susceptible | Susceptible | Susceptible |

H. Post Harvest

| Characteristic | Red Sky | Carnival | Revolution |
|---|---|---|---|
| Pink Rib | Susceptible | Susceptible | Susceptible |
| Russet Spotting | Susceptible | Susceptible | Susceptible |
| Rusty Brown Discoloration | Susceptible | Susceptible | Susceptible |

-continued

| Characteristic | Red Sky | Carnival | Revolution |
|---|---|---|---|
| Internal Rib Necrosis (Blackheart, Gray Rib, Gray Streak) | Susceptible | Susceptible | Susceptible |

VII. ORIGIN AND BREEDING HISTORY OF THE VARIETY VALENTINE

Valentine is a Red Leaf lettuce variety developed from a hand pollinated cross of the red Batavia cultivar Carnival, a Progeny Advanced Genetics variety, and the Dark Lolla Rossa cultivar Revolution. The initial cross was made in a San Joaquin valley research and development seed production field in Year 1. The F1 seed harvested was designated as PSJV032055XPSJV032066. Carnival, a medium sized, open growing, heavily textured single red Batavia lettuce type was selected as a source of improved heavier and thicker leaf texture, increased leaf weight, its slow growth habit, and its adaptability to warmer lettuce production areas and time periods. Revolution was selected for its triple red color, increased resistance to Downy mildew and its more frilled leaf margin. By implementation of single seed descent and the pedigree selection breeding methods we developed a triple red, Downy mildew resistant Red Leaf variety with thicker textured and heavier leaves. Valentine is resistant to multiple pathotypes of Downy mildew, including dm pathotypes 1-5, 7-10 and 17.

Following harvest of the F1 seeds, approximately 50 plants of the F1 seed were immediately planted in a research green house for seed increase late in Year 1. The F2 seed was harvested in mass in the spring of Year 2 and labeled PSJB032392.

A population of roughly 100 F2 plants labeled PSJV043058 was planted in a research and development seed production field in the spring of Year 2. One hundred individual F2 plants were randomly selected and harvested individually when the seed reached maturity. The individual F3 plants harvested were cleaned and processed and labeled in individual envelopes as PSJV043058-1 through PSJV043058-100. One seed from each envelope was removed randomly and placed in a new envelope labeled PAUS043619.

The 100 seeds labeled PAUS043619 were sent to Australia and grown in a research seed production field during the northern hemisphere winter of Year 2 to Year 3. Again, at seed maturity, all 100 plants were harvested, processed and packaged individually. The F4 seed was shipped back to the US, where 100 packets labeled PAUS043619-1 through PAUS043619-100 were received.

Fifty plants from each F4 line were planted in seedling trays, along side parent and standard Red Leaf varieties. After roughly 2 weeks of green house growth the plants were moved out doors to develop their true leaf color and texture. After roughly 40 days of growth the lines were evaluated for uniformity, color, leaf type, leaf frill, leaf thickness and leaf weight. The F4 lines that exhibited the best combination of these traits were selected and noted. The advancements included line number PAUS043619-71.

Roughly 100 seeds of PAUS043619-71 were then planted in a green house research facility, under the designation PSJB054594 in the fall of Year 3. The 100 plants were rogued at the rosette stage of maturity and any off types were removed. The remainder of the plants was allowed to grow to complete seed maturity and the F5 seed was harvested in mass in the spring of Year 4. This F5 line, selected F5 sister lines and the parent lines were grown and evaluated in multiple green house and field trials in Year 4. The lines were evaluated based on uniformity, color, leaf type, leaf frill, leaf thickness and leaf weight. The lines that best demonstrated the combined traits were noted and advanced.

While the trials of the F5 lines were being conducted and evaluated, the F6 seed increase was being conducted simultaneously in a summer Year 4 research seed production field. Line PSJB054594 was redesignated as PSJV065052-b/s, and 1000 plants were planted for seed increase. The F5 line was rogued at multiple stages of development and any noted offtypes were removed. The remaining plants were harvested in mass in the fall of Year 4.

Multiple large scale trials of PSJV065052-b/s, its advanced sister lines and its parent lines were again conducted and evaluated in Year 5. The trials were evaluated, and the lines that expressed the best combination of desired leaf color, leaf type, leaf frill, leaf thickness and leaf weight were advanced, including PSJV065030-b/s.

Again, additional seed increases were made of the lines while the trials were being conducted during the summer of Year 5. Line PSJV065052-b/s was redesignated PSJV075852 and 2000 plants were grown in a research and development seed production field for seed increase. The F7 seed was harvested in mass in the fall of Year 5.

All lines that were advanced from the Year 5 trialing process were then screened for resistance to Downy mildew by a commercial laboratory. Line PSJV075852, along with multiple advanced sister lines were screened. PSJV075852 was determined to be resistant to Downy mildew pathotypes 1-5, 7-10 and 17.

Based on trialing and the disease screening results, the item PSJV075852 was advanced and designated as PX 122 in the fall of Year 5.

PX 122 was again increased in a Year 6 commercial seed production block in the San Joaquin valley. The variety was evaluated and noted to be uniform, stable and free of variants. The F8 seed was harvested in mass in the late summer of Year 5. Additional trialing of F8 seed for was conducted in Year 5 and Year 6.

PX 122 was named 'Valentine' in the fall of Year 5.

As evaluated in seed production and field trials, the F7 and the F8 seed from the variety Valentine has been uniform and stable with out variants.

A. Variety Description Information Valentine

| | |
|---|---|
| Plant Type: | Red Leaf |
| Seed: | |
| Seed Color: | White |
| Light Dormancy: | No |
| Heat Dormancy: | Yes |
| Cotyledons: | |
| Shape of Cotyledons: | Spatulate |
| Shape of Fourth Leaf: | Elongated |
| Length/Width Index of Fourth Leaf: | 22 |
| Apical Margin: | Moderately Dentate |
| Basal Margin: | Moderately Dentate |
| Undulation: | Medium |
| Green Color: | Medium |
| Anthocyanin: | |
| Distribution: | Spotted |
| Rolling: | Present |
| Cupping: | Slight |
| Reflexing: | Apical Margin |
| Mature Leaves: | |

-continued

| Margin: | |
|---|---|
| Incision Depth (Deepest penetration of the margin): | Moderate |
| Indentation (Finest Division of the Margin): | Crenate |
| Undulation of the Apical Margin: | Moderate |
| Green Color: | Medium |
| Anthocyanin | |
| Distribution: | Throughout |
| Size: | Medium |
| Glossiness: | Medium |
| Blistering: | Absent |
| Leaf Thickness: | Thick |
| Trichomes: | Absent |

B. Comparison to Most Similar Variety

| Characteristic | Valentine | Carnival | Revolution |
|---|---|---|---|
| Spread of Frame Leaves | 20 | 26 | 18 |
| Head Diameter (market trimmed with single cup leaf) | N/A | 12 cm | N/A |
| Head Shape | Open | Upright | Open |
| Head Size Class | Small | Medium | Small |
| Head Count per Carton | N/A | N/A | N/A |
| Head Weight | N/A | 450 g | N/A |
| Head Firmness | N/A | N/A | N/A |
| Butt | | | |
| Shape | Pointed | Rounded | Pointed |
| Midrib | Flat | Moderately raised | Flat |
| Core (Stem of Market-trimmed Head) | | | |
| Diameter at the base of the Head | N/A | 4.5 cm | N/A |
| Ratio of Head Diameter/Core Diameter | N/A | 2.6 | N/A |
| Core Height from base of Head to Apex | N/A | 3.5 cm | N/A |
| Number of Days from First Water Date to Seed Stalk Emergence (Summer condition) | 52 | 66 | 48 |
| Bolting Class | Fast | Slow | Fast |
| Height of Mature Seed Stalk | 126 cm | 119 cm | 118 cm |
| Spread of Bolter Plant | 30 cm | 30 cm | 19 cm |
| Bolter Leaves | Curved | Straight | Curved |
| Margin | Dentate | Entire | Dentate |
| Color | Medium Red | Green/red | Dark Red |
| Bolter Habit | | | |
| Terminal Inflorescence | Absent | Absent | Absent |
| Lateral Shoots (above head) | Absent | Absent | Absent |
| Basal Side Shoots | Absent | Absent | Absent |
| Adaptation Regions | | | |

C. Growing Season

| Season | Valentine | Carnival | Revolution |
|---|---|---|---|
| Spring area | All Coastal and Desert regions | All Coastal and Desert regions | All Coastal and Desert regions |
| Summer area | All Coastal regions | All Coastal regions | All Coastal regions |
| Fall area | All Coastal and Desert regions | All Coastal and Desert regions | All Coastal and Desert regions |
| Winter area: | All Desert regions | All Desert regions | All Desert regions |

D. Diseases and Stress Reactions

| Disease or Stress | Valentine | Carnival | Revolution |
|---|---|---|---|
| Virus | | | |
| Big Vein: | Susceptible | Susceptible | Susceptible |
| Lettuce Mosaic: | Resistant | Resistant | Resistant |

E. Fungi/Bacteria

| Fungal/Bacterial | Valentine | Carnival | Revolution |
|---|---|---|---|
| Corky Root Rot (*Pythium* Root Rot): | Susceptible | Susceptible | Susceptible |
| Downy Mildew | Resistant bl 1-5, 7-10 and 17 | Ca I, II, III | bl 1-16, 21, 23 and CA I-VI |
| Powdery Mildew: | Susceptible | Susceptible | Susceptible |
| Sclerotinia Rot: | Susceptible | Susceptible | Susceptible |
| Bacterial Soft Rot (*Pseudomonas* spp. & others): Not tested | Susceptible | Susceptible | Susceptible |
| *Botrytis* (Gray Mold): | Susceptible | Susceptible | Susceptible |
| Other: Corky Root Rot (*Rhizomonas suberifaciens*): | Susceptible | Susceptible | Susceptible |

F. Insects

| Insects | Valentine | Carnival | Revolution |
|---|---|---|---|
| Cabbage Loopers: | Susceptible | Susceptible | Susceptible |
| Root Aphids: | Susceptible | Susceptible | Susceptible |
| Green Peach Aphid: | Susceptible | Susceptible | Susceptible |

G. Physiological/Stress

| Stress | Valentine | Carnival | Revolution |
|---|---|---|---|
| Tipburn | N/A | Resistant | N/A |
| Heat | Susceptible | Resistant | Susceptible |
| Drought | Susceptible | Susceptible | Susceptible |
| Cold | Susceptible | Susceptible | Susceptible |
| Salt | Susceptible | Susceptible | Susceptible |

H. Post Harvest

| Characteristic | Valentine | Carnival | Revolution |
|---|---|---|---|
| Pink Rib | Susceptible | Susceptible | Susceptible |
| Russet Spotting | Susceptible | Susceptible | Susceptible |
| Rusty Brown Discoloration | Susceptible | Susceptible | Susceptible |
| Internal Rib Necrosis (Blackheart, Gray Rib, Gray Streak) | Susceptible | Susceptible | Susceptible |

VIII. ORIGIN AND BREEDING HISTORY OF THE VARIETY RED MORNING

Red Morning is a Red Leaf lettuce variety developed from a hand pollinated cross of the red baby leaf cultivar Galactic, an Enza Zaden variety, and the Red Batavia cultivar Carnival, a Progeny Advanced Genetics variety. The initial cross was made in a San Joaquin valley research and development seed production field in Year 1. The F1 seed harvested was designated as PSJV032057XPSJV032055. Carnival, a medium sized, open growing, heavily textured single red Batavia lettuce type was selected as a source of improved heavier and thicker leaf texture, increased leaf weight, its slow growth habit, and its adaptability to warmer lettuce production areas and time periods. Galactic was selected for its triple red color, increased resistance to Downy mildew and its more frilled leaf margin. By implementation of single seed descent and the pedigree selection breeding methods we developed a triple red, Red Leaf variety with thicker textured and heavier leaves.

Following harvest of the F1 seeds, approximately 50 plants of the F1 seed were immediately planted in a research green house for seed increase late in Year 1. The F2 seed was harvested in mass in the spring of Year 2 and labeled PSJB032393.

A population of roughly 100 F2 plants labeled PSJV043059 was planted in a research and development seed production field in the spring of Year 2. One hundred individual F2 plants were randomly selected and harvested individually when the seed reached maturity. The individual F3 plants harvested were cleaned and processed and labeled in individual envelopes as PSJV043059-1 through PSJV043059-100. One seed from each envelope was removed randomly and placed in a new envelope labeled PAUS043620.

The 100 seeds labeled PAUS043620 were sent to Australia and grown in a research seed production field during the northern hemisphere winter of Year 2 to Year 3. Again, at seed maturity, all 100 plants were harvested, processed and packaged individually. The F4 seed was shipped back to the US, where 100 packets labeled PAUS043620-1 through PAUS043620-100 were received.

Fifty plants from each F4 line were planted in seedling trays, along side parent and standard Red Leaf varieties. After roughly 2 weeks of green house growth the plants were moved out doors to develop their true leaf color and texture. After roughly 40 days of growth the lines were evaluated for uniformity, color, leaf type, leaf frill, leaf thickness and leaf weight. The F4 lines that exhibited the best combination of these traits were selected and noted. The advancements included line number PAUS043620-5.

Roughly 100 seeds of PAUS043620-5 were then planted in a green house research facility, under the designation PSJB054601 in the fall of Year 3. The 100 plants were rogued at the rosette stage of maturity and any off types were removed. The remainder of the plants was allowed to grow to complete seed maturity and the F5 seed was harvested in mass in the spring of Year 4. This F5 line, selected F5 sister lines and the parent lines were grown and evaluated in multiple green house and field trials in Year 4. The lines were evaluated based on uniformity, color, leaf type, leaf frill, leaf thickness and leaf weight. The lines that best demonstrated the combined traits were noted and advanced.

While the trials of the F5 lines were being conducted and evaluated, the F6 seed increase was being conducted simultaneously in a summer Year 4 research seed production field. Line PSJB054601 was redesignated as PSJV065065, and 1000 plants were planted for seed increase. The F5 line was rogued at multiple stages of development and any noted offtypes were removed. The remaining plants were harvested in mass in the fall of Year 4.

Multiple large scale trials of PSJV065065, its advanced sister lines and its parent lines were again conducted and evaluated in Year 5. The trials were evaluated, and the lines that expressed the best combination of desired leaf color, leaf type, leaf frill, leaf thickness and leaf weight were advanced, including PSJV065030.

Again, additional seed increases were made of the lines while the trials were being conducted during the summer of Year 5. Line PSJV065065 was redesignated PSJV075855 and 2000 plants were grown in a research and development seed production field for seed increase. The F7 seed was harvested in mass in the fall of Year 5.

Based on trialing and the disease screening results, the item PSJV075855 was advanced and designated as PX 125 in the fall of Year 5.

PX 125 was again increased in a Year 6 commercial seed production block in the San Joaquin valley. The variety was evaluated and noted to be uniform, stable and free of variants. The F8 seed was harvested in mass in the late summer of Year 6. Additional trialing of F8 seed for was conducted in Year 6 and Year 7.

PX 125 was named 'Red Morning' in the fall of Year 6.

As evaluated in seed production and field trials, the F7 and the F8 seed from the variety Red Morning has been uniform and stable with out variants.

A. Variety Description Information Red Morning

| | |
|---|---|
| Plant Type: | Red Leaf |
| Seed: | |
| Seed Color: | White |
| Light Dormancy: | No |
| Heat Dormancy: | Yes |
| Cotyledons: | |
| Shape of Cotyledons: | Spatulate |
| Shape of Fourth Leaf: | Elongated |
| Length/Width Index of Fourth Leaf: | 18 |
| Apical Margin: | Moderately Dentate |
| Basal Margin: | Moderately Dentate |
| Undulation: | Medium |
| Green Color: | Medium |
| Anthocyanin: | |
| Distribution: | Spotted |
| Rolling: | Present |
| Cupping: | Slight |
| Reflexing: | Apical Margin |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Medium |
| Anthocyanin | |
| Distribution: | Throughout |
| Size: | Medium |
| Glossiness: | Medium |
| Blistering: | Absent |
| Leaf Thickness: | Thick |
| Trichomes: | Absent |

B. Comparison to Most Similar Variety

| Characteristic | Red Morning | Carnival | Revolution |
|---|---|---|---|
| Spread of Frame Leaves | 22 | 26 | 18 |
| Head Diameter (market trimmed with single cup leaf) | N/A | 12 cm | N/A |
| Head Shape | Open | Upright | Open |
| Head Size Class | Small | Medium | Small |
| Head Count per Carton | N/A | N/A | N/A |
| Head Weight | N/A | 450 g | N/A |
| Head Firmness | N/A | N/A | N/A |
| Butt | | | |
| Shape | Pointed | Rounded | Pointed |
| Midrib | Flat | Moderately raised | Flat |
| Core (Stem of Market-trimmed Head) | | | |
| Diameter at the base of the Head | N/A | 4.5 cm | N/A |
| Ratio of Head Diameter/Core Diameter | N/A | 2.6 | N/A |
| Core Height from base of Head to Apex | N/A | 3.5 cm | N/A |
| Number of Days from First Water Date to Seed Stalk Emergence (Summer condition) | 48 | 66 | 48 |
| Bolting Class | Fast | Slow | Fast |
| Height of Mature Seed Stalk | 119 cm | 119 cm | 118 cm |
| Spread of Bolter Plant | 27 cm | 30 cm | 19 cm |
| Bolter Leaves | Curved | Straight | Curved |
| Margin | Dentate | Entire | Dentate |
| Color | Medium Red | Green/red | Dark Red |
| Bolter Habit | | | |
| Terminal Inflorescence | Absent | Absent | Absent |
| Lateral Shoots (above head) | Absent | Absent | Absent |
| Basal Side Shoots | Absent | Absent | Absent |
| Adaptation Regions | | | |

C. Growing Season

| Season | Red Morning | Carnival | Revolution |
|---|---|---|---|
| Spring area | All Coastal and Desert regions | All Coastal and Desert regions | All Coastal and Desert regions |
| Summer area | All Coastal regions | All Coastal regions | All Coastal regions |
| Fall area | All Coastal and Desert regions | All Coastal and Desert regions | All Coastal and Desert regions |
| Winter area: | All Desert regions | All Desert regions | All Desert regions |

D. Diseases and Stress Reactions

| Disease or Stress | Red Morning | Carnival | Revolution |
|---|---|---|---|
| Virus | | | |
| Big Vein: | Susceptible | Susceptible | Susceptible |
| Lettuce Mosaic: | Resistant | Resistant | Resistant |

E. Fungi/Bacteria

| Fungal/Bacterial | Red Morning | Carnival | Revolution |
|---|---|---|---|
| Corky Root Rot (*Pythium* Root Rot): | Susceptible | Susceptible | Susceptible |
| Downy Mildew | Resistant bl 1-5, 7-10 and 17 | Ca I, II, III | bl 1-16, 21, 23 and CA I-VI |
| Powdery Mildew: | Susceptible | Susceptible | Susceptible |
| *Sclerotinia* Rot: | Susceptible | Susceptible | Susceptible |
| Bacterial Soft Rot (*Pseudomonas* spp. & others): | Not tested | | |
| *Botrytis* (Gray Mold): | Susceptible | Susceptible | Susceptible |
| Other: Corky Root Rot (*Rhizomonas suberifaciens*): | Susceptible | Susceptible | Susceptible |

F. Insects

| Insects | Red Morning | Carnival | Revolution |
|---|---|---|---|
| Cabbage Loopers: | Susceptible | Susceptible | Susceptible |
| Root Aphids: | Susceptible | Susceptible | Susceptible |
| Green Peach Aphid: | Susceptible | Susceptible | Susceptible |

G. Physiological/Stress

| Stress | Red Morning | Carnival | Revolution |
|---|---|---|---|
| Tipburn | N/A | Resistant | N/A |
| Heat | Susceptible | Resistant | Susceptible |
| Drought | Susceptible | Susceptible | Susceptible |
| Cold | Susceptible | Susceptible | Susceptible |
| Salt | Susceptible | Susceptible | Susceptible |

H. Post Harvest

| Characteristic | Red Morning | Carnival | Revolution |
|---|---|---|---|
| Pink Rib | Susceptible | Susceptible | Susceptible |
| Russet Spotting | Susceptible | Susceptible | Susceptible |
| Rusty Brown Discoloration | Susceptible | Susceptible | Susceptible |
| Internal Rib Necrosis (Blackheart, Gray Rib, Gray Streak) | Susceptible | Susceptible | Susceptible |

IX. ORIGIN AND BREEDING HISTORY OF THE VARIETY SUN RISE

Sun Rise is a Red Leaf lettuce variety developed from a hand pollinated cross of the red Batavia cultivar Carnival, a Progeny Advanced Genetics variety, and the Dark Lolla Rossa cultivar Revolution. The initial cross was made in a San Joaquin valley research and development seed production field in Year 1. The F1 seed harvested was designated as PSJV032055XPSJV032066. Carnival, a medium sized, open growing, heavily textured single red Batavia lettuce type was selected as a source of improved heavier and thicker leaf texture, increased leaf weight, its slow growth habit, and its adaptability to warmer lettuce production areas and time periods. Revolution was selected for its triple red color, increased resistance to Downy mildew and its more frilled leaf margin.

By implementation of single seed descent and the pedigree selection breeding methods we developed a triple red, Downy mildew resistant Red Leaf variety with thicker textured and heavier leaves. Sun Rise is resistant to multiple pathotypes of Downy mildew, including dm pathotypes 1-5, 7-10 and 17.

Following harvest of the F1 seeds, approximately 50 plants of the F1 seed were immediately planted in a research green house for seed increase late in Year 1. The F2 seed was harvested in mass in the spring of Year 2 and labeled PSJB032392.

A population of roughly 100 F2 plants labeled PSJV043058 was planted in a research and development seed production field in the spring of Year 2. One hundred individual F2 plants were randomly selected and harvested individually when the seed reached maturity. The individual F3 plants harvested were cleaned and processed and labeled in individual envelopes as PSJV043058-1 through PSJV043058-100. One seed from each envelope was removed randomly and placed in a new envelope labeled PAUS043619.

The 100 seeds labeled PAUS043619 were sent to Australia and grown in a research seed production field during the northern hemisphere winter of Year 2 to Year 3. Again, at seed maturity, all 100 plants were harvested, processed and packaged individually. The F4 seed was shipped back to the US, where 100 packets labeled PAUS043619-1 through PAUS043619-100 were received.

Fifty plants from each F4 line were planted in seedling trays, along side parent and standard Red Leaf varieties. After roughly 2 weeks of green house growth the plants were moved out doors to develop their true leaf color and texture. After roughly 40 days of growth the lines were evaluated for uniformity, color, leaf type, leaf frill, leaf thickness and leaf weight. The F4 lines that exhibited the best combination of these traits were selected and noted. The advancements included line number PAUS043619-71.

Roughly 100 seeds of PAUS043619-71 were then planted in a green house research facility, under the designation PSJB054594 in the fall of Year 3. The 100 plants were rogued at the rosette stage of maturity and any off types were removed. The remainder of the plants was allowed to grow to complete seed maturity and the F5 seed was harvested in mass in the spring of Year 4. This F5 line, selected F5 sister lines and the parent lines were grown and evaluated in multiple green house and field trials in Year 4. The lines were evaluated based on uniformity, color, leaf type, leaf frill, leaf thickness and leaf weight. The lines that best demonstrated the combined traits were noted and advanced.

While the trials of the F5 lines were being conducted and evaluated, the F6 seed increase was being conducted simultaneously in a summer Year 4 research seed production field. Line PSJB054594 was redesignated as PSJV065052-w/s, and 1000 plants were planted for seed increase. The F5 line was rogued at multiple stages of development and any noted offtypes were removed. The remaining plants were harvested in mass in the fall of Year 4.

Multiple large scale trials of PSJV065052-w/s, its advanced sister lines and its parent lines were again conducted and evaluated in Year 5. The trials were evaluated, and the lines that expressed the best combination of desired leaf color, leaf type, leaf frill, leaf thickness and leaf weight were advanced, including PSJV065052-w/s.

Again, additional seed increases were made of the lines while the trials were being conducted during the summer of Year 5. Line PSJV065052-w/s was redesignated PSJV075853 and 2000 plants were grown in a research and development seed production field for seed increase. The F7 seed was harvested in mass in the fall of Year 5.

All lines that were advanced from the Year 5 trialing process were then screened for resistance to Downy mildew by a commercial laboratory. Line PSJV075853, along with multiple advanced sister lines were screened. PSJV075853 was determined to be resistant to Downy mildew pathotypes 1-5, 7-10 and 17.

Based on trialing and the disease screening results, the item PSJV075853 was advanced and designated as PX 123 in the fall of Year 5.

PX 123 was again increased in a Year 6 commercial seed production block in the San Joaquin valley. The variety was evaluated and noted to be uniform, stable and free of variants. The F8 seed was harvested in mass in the late summer of Year 6. Additional trialing of F8 seed for was conducted in Year 6 and Year 7.

PX 123 was named 'Sun Rise' in the fall of Year 6.

As evaluated in seed production and field trials, the F7 and the F8 seed from the variety Sun Rise has been uniform and stable with out variants.

A. Variety Description Information Sun Rise

| | |
|---|---|
| Plant Type: | Red Leaf |
| Seed: | |
| Seed Color: | White |
| Light Dormancy: | No |
| Heat Dormancy: | Yes |
| Cotyledons: | |
| Shape of Cotyledons: | Spatulate |
| Shape of Fourth Leaf: | Elongated |
| Length/Width Index of Fourth Leaf: | 22 |
| Apical Margin: | Moderately Dentate |
| Basal Margin: | Moderately Dentate |
| Undulation: | Medium |
| Green Color: | Medium |
| Anthocyanin: | |
| Distribution: | Spotted |
| Rolling: | Present |
| Cupping: | Slight |
| Reflexing: | Apical Margin |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Medium |
| Anthocyanin | |
| Distribution: | Throughout |
| Size: | Medium |
| Glossiness: | Medium |
| Blistering: | Absent |
| Leaf Thickness: | Thick |
| Trichomes: | Absent |

B. Comparison to Most Similar Variety

| Characteristic | Sun Rise | Carnival | Revolution |
|---|---|---|---|
| Spread of Frame Leaves | 19 | 26 | 18 |
| Head Diameter (market trimmed with single cup leaf) | N/A | 12 cm | N/A |
| Head Shape | Open | Upright | Open |
| Head Size Class | Small | Medium | Small |

-continued

| Characteristic | Sun Rise | Carnival | Revolution |
|---|---|---|---|
| Head Count per Carton | N/A | N/A | N/A |
| Head Weight | N/A | 450 g | N/A |
| Head Firmness | N/A | N/A | N/A |
| Butt | | | |
| Shape | Pointed | Rounded | Pointed |
| Midrib | Flat | Moderately raised | Flat |
| Core (Stem of Market-trimmed Head) | | | |
| Diameter at the base of the Head | N/A | 4.5 cm | N/A |
| Ratio of Head Diameter/Core Diameter | N/A | 2.6 | N/A |
| Core Height from base of Head to Apex | N/A | 3.5 cm | N/A |
| Number of Days from First Water Date to Seed Stalk Emergence (Summer condition) | 53 | 66 | 48 |
| Bolting Class | Fast | Slow | Fast |
| Height of Mature Seed Stalk | 1110 cm | 119 cm | 118 cm |
| Spread of Bolter Plant | 24 cm | 30 cm | 19 cm |
| Bolter Leaves | Curved | Straight | Curved |
| Margin | Dentate | Entire | Dentate |
| Color | Medium Red | Green/red | Dark Red |
| Bolter Habit | | | |
| Terminal Inflorescence | Absent | Absent | Absent |
| Lateral Shoots (above head) | Absent | Absent | Absent |
| Basal Side Shoots | Absent | Absent | Absent |
| Adaptation Regions | | | |

C. Growing Season

| Season | Sun Rise | Carnival | Revolution |
|---|---|---|---|
| Spring area | All Coastal and Desert regions | All Coastal and Desert regions | All Coastal and Desert regions |
| Summer area | All Coastal regions | All Coastal regions | All Coastal regions |
| Fall area | All Coastal and Desert regions | All Coastal and Desert regions | All Coastal and Desert regions |
| Winter area: | All Desert regions | All Desert regions | All Desert regions |

D. Diseases and Stress Reactions

| Disease or Stress | Sun Rise | Carnival | Revolution |
|---|---|---|---|
| Virus | | | |
| Big Vein: | Susceptible | Susceptible | Susceptible |
| Lettuce Mosaic: | Resistant | Resistant | Resistant |

E. Fungi/Bacteria

| Fungal/Bacterial | Sun Rise | Carnival | Revolution |
|---|---|---|---|
| Corky Root Rot (*Pythium* Root Rot): | Susceptible | Susceptible | Susceptible |
| Downy Mildew | Susceptible | Ca I, II, III | bl 1-16, 21, 23 and CA I-VI |
| Powdery Mildew: | Susceptible | Susceptible | Susceptible |
| *Sclerotinia* Rot: | Susceptible | Susceptible | Susceptible |
| Bacterial Soft Rot (*Pseudomonas* spp. & others): Not tested | Susceptible | Susceptible | Susceptible |
| *Botrytis* (Gray Mold): | Susceptible | Susceptible | Susceptible |
| Other: Corky Root Rot (*Rhizomonas suberifaciens*): | Susceptible | Susceptible | Susceptible |

F. Insects

| Insects | Sun Rise | Carnival | Revolution |
|---|---|---|---|
| Cabbage Loopers: | Susceptible | Susceptible | Susceptible |
| Root Aphids: | Susceptible | Susceptible | Susceptible |
| Green Peach Aphid: | Susceptible | Susceptible | Susceptible |

G. Physiological/Stress

| Stress | Sun Rise | Carnival | Revolution |
|---|---|---|---|
| Tipburn | N/A | Resistant | N/A |
| Heat | Susceptible | Resistant | Susceptible |
| Drought | Susceptible | Susceptible | Susceptible |
| Cold | Susceptible | Susceptible | Susceptible |
| Salt | Susceptible | Susceptible | Susceptible |

H. Post Harvest

| Characteristic | Sun Rise | Carnival | Revolution |
|---|---|---|---|
| Pink Rib | Susceptible | Susceptible | Susceptible |
| Russet Spotting | Susceptible | Susceptible | Susceptible |
| Rusty Brown Discoloration | Susceptible | Susceptible | Susceptible |
| Internal Rib Necrosis (Blackheart, Gray Rib, Gray Streak) | Susceptible | Susceptible | Susceptible |

X. BREEDING AND SELECTION

The present invention is further directed to the use of Red Sky, Valentine, Red Morning, and Sun Rise lettuce varieties in the breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading Red Leaf lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen are washed off with enough pressure to dislodge the pollen grains, but not enough to damage the style. Excess water is dried off with clean paper towels. About 30 minutes later the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to isolate lettuce new lettuce lines. One or more lettuce seeds are planted, the plants are grown and single plant selections are made of plants with desired characteristics. Such characteristics may include improved head and frame size, deeper or darker green leaf color, etc. Seed from the single plant selections are harvested; separated from seeds of the other plants in the field and re-planted. The plants from the selected seed are monitored to determine if they exhibit the desired characteristics from the originally selected line. Selection work is continued over multiple generations to increase the uniformity and size of new line.

XI. DEPOSIT INFORMATION

Applicants have made available to the public without restriction a deposit of at least 2500 seeds of lettuce variety Red Sky with the American Type Culture Collection (ATCC), 10801 University Boulevard, Manassas, Va. 20110 with a deposit on Feb. 8, 2011 which has been assigned ATCC number PTA-11666.

Applicants have made available to the public without restriction a deposit of at least 2500 seeds of lettuce variety Valentine with the American Type Culture Collection (ATCC), 10801 University Boulevard, Manassas, Va. 20110 with a deposit on Feb. 8, 2011 which has been assigned ATCC number PTA-11668.

Applicants have made available to the public without restriction a deposit of at least 2500 seeds of lettuce variety Red Morning with the American Type Culture Collection (ATCC), 10801 University Boulevard, Manassas, Va. 20110 with a deposit on Feb. 8, 2011 which has been assigned ATCC number PTA-11669.

Applicants have made available to the public without restriction a deposit of at least 2500 seeds of lettuce variety Sun Rise with the American Type Culture Collection (ATCC), 10801 University Boulevard, Manassas, Va. 20110 with a deposit on Feb. 8, 2011 which has been assigned ATCC number PTA-11667.

The deposits will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Example.

EXAMPLE 1

Comparative Analysis

Red Sky, Valentine, Red Morning, and Sun Rise are new and distinct varieties of Red Leaf lettuce that most closely resemble the commercial variety Galactic. Red Sky, Valentine, Red Morning, and Sun Rise are triple red, Red Leaf lettuce varieties grown for spring mix and adapted to all the harvest periods of the California coastal growing region, the desert south west growing region of California and Arizona, and the Huron lettuce production region of California. Red Sky, Valentine, Red Morning, and Sun Rise are triple red in color, resistant to multiple pathotypes of Downy mildew, and possess an improved thicker leaf texture, providing increased leaf weight. Red Sky, Valentine, Red Morning, and Sun Rise are most similar to the lettuce variety Revolution, but have a smoother and less frilled leaf margin, a more elongated leaf, and a thicker heavier leaf.

Red Sky, Valentine, Red Morning, and Sun Rise are produced as a spring mix lettuce variety where as the parent variety Carnival is produced only as a full grown lettuce type. Similar to Carnival, the varieties Red Sky, Valentine, Red Morning, and Sun Rise have a thicker leaf texture, a characteristic of Batavia lettuce types. But whereas Carnival has only light anthocyanin concentration giving it a lighter red color, the varieties Red Sky, Valentine, Red Morning, and Sun Rise have a heavier concentration, resulting in a deeper red color. Whereas Carnival has a broad leaf, with a broad petiole, the varieties Red Sky, Valentine, Red Morning, and Sun Rise have an elongated leaf with a narrow and elongated petiole. The varieties Red Sky, Valentine, Red Morning, and Sun Rise also possess increased resistance to Downey mildew (Dm) as compared to Carnival. Whereas Carnival is resistant to Dm races I, II, and III, Red Sky is resistant to bl races 1-16, 21 and 24, and Ca races I-VII; Valentine and Red Morning are resistant to bl races 1-5, 7-10 and 17; and Sun Rise is susceptible to all races.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

The invention claimed is:
1. *Lactuca sativa* seed designated as Red Sky having ATCC Accession Number PTA-11666.
2. A *Lactuca sativa* plant produced by growing the seed of claim 1.
3. A *Lactuca sativa* plant having all the physiological and morphological characteristics of the *Lactuca sativa* plant of claim 2.
4. An $F_1$ hybrid *Lactuca sativa* plant having Red Sky as a parent where Red Sky is grown from the seed of claim 1.
5. Pollen or tissue culture of the plant of claim 2.
6. A method of selecting lettuce, comprising
    a) growing more than one plant from the seed of claim 1, and
    b) selecting a plant from step a).

7. *Lactuca sativa* seed designated as Valentine having ATCC Accession Number PTA-11668.

8. A *Lactuca sativa* plant produced by growing the seed of claim 7.

9. A *Lactuca sativa* plant having all the physiological and morphological characteristics of the *Lactuca sativa* plant of claim 8.

10. An $F_1$ hybrid *Lactuca sativa* plant having Valentine as a parent where Valentine is grown from the seed of claim 7.

11. Pollen or tissue culture of the plant of claim 8.

12. A method of selecting lettuce, comprising
 a) growing more than one plant from the seed of claim 7, and
 b) selecting a plant from step a).

13. *Lactuca sativa* seed designated as Red Morning having ATCC Accession Number PTA-11669.

14. A *Lactuca sativa* plant produced by growing the seed of claim 13.

15. A *Lactuca sativa* plant having all the physiological and morphological characteristics of the *Lactuca sativa* plant of claim 14.

16. An $F_1$ hybrid *Lactuca sativa* plant having Red Morning as a parent where Red Morning is grown from the seed of claim 13.

17. Pollen or tissue culture of the plant of claim 14.

18. A method of selecting lettuce, comprising
 a) growing more than one plant from the seed of claim 13, and
 b) selecting a plant from step a).

19. *Lactuca sativa* seed designated as Sun Rise having ATCC Accession Number PTA-11667.

20. A *Lactuca sativa* plant produced by growing the seed of claim 19.

21. A *Lactuca sativa* plant having all the physiological and morphological characteristics of the *Lactuca sativa* plant of claim 20.

22. An $F_1$ hybrid *Lactuca sativa* plant having Sun Rise as a parent where Sun Rise is grown from the seed of claim 19.

23. Pollen or tissue culture of the plant of claim 20.

24. A method of selecting lettuce, comprising
 a) growing more than one plant from the seed of claim 19, and
 b) selecting a plant from step a).

* * * * *